US006436993B1

(12) United States Patent
Evans et al.

(10) Patent No.: US 6,436,993 B1
(45) Date of Patent: *Aug. 20, 2002

(54) USE OF RAR ANTAGONISTS AS MODULATORS OF HORMONE MEDIATED PROCESSES

(75) Inventors: Ronald M. Evans, La Jolla; Peter J. Tontonoz, Los Angeles; Laszlo Nagy, San Diego, all of CA (US)

(73) Assignee: The Salk Institute for Biological Studies, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/352,816

(22) Filed: Jul. 13, 1999

(51) Int. Cl.[7] .................. A61K 31/20; A61K 31/455; A61K 31/38

(52) U.S. Cl. ............... 514/549; 514/356; 514/443; 514/448; 514/559; 514/475; 514/560

(58) Field of Search ................. 514/356, 239.2, 514/311, 443, 448, 559, 549

(56) References Cited

U.S. PATENT DOCUMENTS

| | | | | |
|---|---|---|---|---|
| 5,212,303 A | * | 5/1993 | Shroot et al. | 544/69 |
| 5,574,036 A | * | 11/1996 | Bernardon et al. | 514/239.2 |
| 5,696,104 A | * | 12/1997 | Demarchez et al. | 514/167 |
| 5,702,710 A | | 12/1997 | Charpentier et al. | 424/401 |
| 5,721,103 A | | 2/1998 | Boehm et al. | 435/7.1 |
| 5,723,666 A | | 3/1998 | Vuligonda et al. | 564/253 |
| 5,728,846 A | | 3/1998 | Vuligonda et al. | 549/16 |
| 5,741,896 A | | 4/1998 | Vuligonda et al. | 534/860 |
| 5,747,530 A | | 5/1998 | Charpentier et al. | 514/468 |
| 5,760,276 A | | 6/1998 | Beard et al. | 560/102 |
| 5,763,635 A | | 6/1998 | Vuligonda et al. | 556/462 |
| 5,767,148 A | * | 6/1998 | Michel et al. | 514/467 |
| 5,770,378 A | | 6/1998 | Hwang et al. | 435/7.1 |
| 5,770,382 A | | 6/1998 | Hwang et al. | 435/7.1 |
| 5,770,383 A | | 6/1998 | Hwang et al. | 435/7.1 |
| 5,773,594 A | | 6/1998 | Johnson et al. | 534/298 |
| 5,780,676 A | * | 7/1998 | Boehm et al. | 562/490 |
| 5,786,379 A | * | 7/1998 | Bernardon | |
| 5,798,354 A | * | 8/1998 | Bernardon et al. | 514/239.2 |
| 5,808,124 A | | 9/1998 | Beard et al. | 556/419 |
| 5,827,500 A | * | 10/1998 | Demarchez et al. | 424/9.1 |
| 5,849,798 A | | 12/1998 | Charpentier et al. | 514/456 |
| 5,877,342 A | | 3/1999 | Bernardon et al. | 560/102 |
| 5,952,382 A | * | 9/1999 | Bernardon | 514/569 |
| 5,973,007 A | * | 10/1999 | Demarchez et al. | 514/568 |
| 5,990,163 A | * | 11/1999 | Evans et al. | 514/549 |
| 5,998,654 A | * | 12/1999 | Boehm et al. | 560/45 |
| 6,004,987 A | * | 12/1999 | Demarchez et al. | 514/356 |
| 6,005,007 A | * | 12/1999 | Farmer et al. | |
| 6,008,204 A | * | 12/1999 | Klein et al. | 514/63 |
| 6,031,149 A | * | 2/2000 | Chambon et al. | 800/2 |
| 6,068,976 A | * | 5/2000 | Briggs et al. | 435/6 |
| 6,083,973 A | * | 7/2000 | Belloni | 514/432 |
| 6,083,977 A | * | 7/2000 | Boehm et al. | 514/457 |
| 6,130,230 A | * | 10/2000 | Chambon et al. | 514/311 |

FOREIGN PATENT DOCUMENTS

| | | | |
|---|---|---|---|
| EP | 0776885 B1 | 11/1996 | |
| WO | WO 97/10819 | 3/1997 | ....... A61K/31/19 |
| WO | WO 98/13065 | 4/1998 | ....... A61K/39/15 |
| WO | WO 99/15520 | 1/1999 | ....... C07D/319/20 |

OTHER PUBLICATIONS

Agarwal et al., "AGN193109 Is a Highly Effective Antagonist of Retinoid Action in Human Ectocervical Epithelial Cells," *The Journal of Biological Chemistry*, 271 (21): 12209–12212, (1996).

Anzano et al., "Prevention of Breast Cancer in the Rat with 9-cis-Retinoic Acid as a Single Agent and in Combination with Tamoxifen," *Cancer Research*, 54:4614–4617, (1994).

Apfel et al., "Enhancement of HL-60 Differentiation by a New Class of Retinoids with Selective Activity on Retiinoid X. Receptor," *The Journal of Biological Chemistry*, 270 (51):30765–30772, (1995).

Beard et al., "Synthesis and Structure–Activity Relationships of Retinoid X Receptor Selective Diaryl Sulfide Analogs of Retinoic Acid," *J. Med. Chem.*, 39: 3556–3563, (1996).

Berger et al., "Novel Preoxisome Proliferator–activated Receptor (PPAR) γ and PPARδ Ligands Produce Distinct Biological Effects," *The Journal of Biological Chemistry*, 274 (10): 6718–6725, (1999).

Bischoff et al., "Beyond Tamoxifen: The Retinoid X Receptor–selective Ligand LGD1069 (TARGRETIN) Causes Complete Regression of Mammary Carcinoma[1]," *Cancer Research*, pp. 479–484, (1998).

Blumberg et al., "BXR, an embryonic orphan nuclear receptor activated by a novel class of endogenous benzoate metabolites," *Genes and Development*, pp. 1269–1277, (1998).

Chen et al., "SMRT isoforms mediate repression and antirepression of nuclear receptor heterodimers," *PNAS*, pp. 7567–7571, (1996).

(List continued on next page.)

*Primary Examiner*—William Jarvis
*Assistant Examiner*—Vickie Kim
(74) *Attorney, Agent, or Firm*—Stephen E. Reiter; Foley & Lardner

(57) ABSTRACT

In accordance with the present invention, it has been discovered that retinoic acid receptor (RAR) antagonists are capable of modulating processes mediated by other members of the steroid/thyroid hormone receptor superfamily, including permissive receptors such as PPARs (e.g., PPARα, PPARδ and PPARγ). Indeed, it has been discovered that RAR antagonists, in combination with agonists for members of the steroid/thyroid hormone receptor superfamily, are capable of inducing and/or enhancing processes mediated by such members.

14 Claims, 3 Drawing Sheets

OTHER PUBLICATIONS

Chen et al., "RAR–specific agonist/antagonists which dissociate transactivation and AP1 transrepression inhibit anchorage–independent cell proliferation," *The EMBO Journal*, 14 (6): 1187–1197, (1995).

Collins et al., "N–(2–Benzoylphenyl)–L–tyrosine PPARγ Agonists. 2. Structure–Activity Relationship and Optimization of the Phenyl Alkyl Ether Moiety," *J. Med. Chem.*, 41: 5037–5054, (1998).

Eckhardt & Schmitt, "A retinoic acid receptor α antagonist counteracts retinoid teratogenicity in vitro and reduced incidence and/or severity of malformations in vivo," *Toxicology Letters*, 70: 299–308, (1994).

Forman et al., "Hypolipidemic drugs, polyunsaturated fatty acids, and eicosaniods are ligands for peroxisome proliferator–activated receptors α and δ," *PNAS*, 94: 4312–4317, (1997).

Formon et al., "15–Deoxy–$\blacktriangle^{12}$, $^1$—Prostaglandin J2 Is a Ligand for the Adipocyte Determination Factor PPARγ," *Cell*, 83: 803–812, (1995).

Fujita & Mitsuhashi, "Differential Regulation of Ligand–Dependent and Ligand–Independent Functions of the Mouse Retinoid X Receptor β by Alternative Splicing," *Biochemical and Biophysical Research Communications*, 255: 625–630, (1999).

Gottardis et al., "Chemoprevention of Mammary Carcinoma by LGD1069 (Targretin): An RXR–selective Ligand," *Cancer Research*, 56: 5566–5570, (1996).

Heyman et al., "9–Cis Retinoic Acid Is a High Affinity Ligand for the Retinoid X Receptor" *Cell*, 68: 397–406, (1992).

Hibi et al., "Syntheses and Structure–Activity Relationships of Novel Retinoid X Receptor Agonists," *J. Med. Chem.*, 41: 3245–3252, (1998).

Iijima et al., "Dicarba–closo–dodecaboranes as a Pharmacophore. Retinoidal Antagonists and Potential Agonists," *Chem. Pharm. Bull.*, 47 (3): 398–404, (1999).

Issemann & Green, "Activation of a member of the steroid hormone receptor superfamily by peroxisome proliferators," *Nature*, 347: 645–650, (1990).

Issemann et al., "The retinoid X receptor enhances the function of the peroxisome proliferator activated receptor," *Biochimie*, 75: 251–256, (1990).

Janowski et al., "Structural requirements of ligands for the oxysterol live X receptors LXRχ and LXRβ" *PNAS Online*, 96 (1): 266–271, (1999).

Jiang et al., "Diminshed Teratogenicity of Retinoid X Receptor–Selective Synthetic Retinoids," *Biochemical Pharmacology*, 50 (5): 669–676, (1995).

Johnson et al., "High Affinity retinoic Acid Receptor Antagonists: Analogs of AGN 193109," *Bioorganic & Medicinal Chemistry Letters*, 9: 573–576, (1999).

Johnson et al., "Synthesis and Characterization of a Highly Potent and Effective Antagonist of Retinoic Acid Receptors," *J. Med. Chem.*, 38: 4764–4767, (1995).

H. Kagechika, "Novel Synthetic Retinoid Agonists and Antagonists," *Reviews* 114(11):847–862 (1994).

Keidel et al., "Different Agonist– and Antagonist–Induced Conformational Changes in Retinoic Acid Receptors Analyzed by Protease Mapping," *Molecular and Cellular Biology*, pp. 287–298, (1994).

Kliewer et al., "A Prostaglandin J$^2$ Metabolite Binds Peroxisome Proliferator–Activated Receptor γ and Promotes Adipocyte Differentiation," *Cell*, 83: 813–819, (1995).

Kliewer et al., "Convergence of 9–cis retinoic acid and peroxisome proliferator signalling pathways through heterodimer formation of their receptors," *Letters to Nature*, 358: 771–774, (1992).

Kliewer et al., "Retinoid X receptor interacts with nuclear receptors in retinoic acid, thyroid hormone and vitamin D3 signalling," *Nature*, 355: 446–449, (1992).

Komers and Vrana, "Thiazolidinediones—Tools for the Research of Metabolic Syndrome X," *Physiol. Res.* 47: 215–225 (1998).

Latruffe & Vamecq, "Peroxisome proliferators and peroxisome proliferator activated receptors (PPARs) as regulators of lipid metabolism," *Biochimie*, 79: 81–94, (1997).

Lee et al., "A Novel Class of Retinoid Antagonists and Their Mechanism of Action," *The Journal of Biological Chemistry*, 271 (20): 11897–11903, (1996).

Leid et al., "Purification, Cloning, and RXR Identity of the HeLa Cell Factor with Which RAR or TR Heterodimerizes to Bind Target Sequences Efficiently," *Cell*, 68: 377–395, (1992).

Lemotte et al., "Phytanic acid is a retinoid X receptor ligand," *Eur. J. Biochem.*, 236: 328–333, (1996).

Li et al., "Identification of a Novel Class of Retinoic Acid Receptor β–Selective Retinoid Antagonists and Their Inhibitory Effects on AP–1 Activity and Retinoic Acid–induced Apoptosis in Human Breast Cancer Cells," *The Journal of Biological Chemistry*, 274 (22): 15360–15366, (1999).

Mangelsdorf et al., "A Direct Repeat in the Cellular Retinol–Binding Protein Type II Gene Confers Differential Regulation by RXR and RAR," *Cell*, 66: 555–561, (1991).

Mangelsdorf & Evans, "The RXR Heterodimers and Orphan Receptors," *Cell*, 83: 841–850, (1995).

Marks et al., "H–2RIIBP (RXRβ) heterodimerization provides a mechanism for combinatorial diveristy in the regulation of retinoic acid and thyroid hormone responsive genes," *The EMBO Journal*, 11 (4): 1419–1435, (1992).

Mascrez, et al., "The RXRα ligant–dependent activation function 2 (AF–2) is important for mouse development," *Development* 125:4601–4707 (1998).

Meister et al., "Antiproliferative Activity and Apoptosis Induced by Retinoic Acid Receptor–γ Selectively Binding Retinoids in Neuroblastoma," *Anticancer Research*, 18: 1777–1786, (1998).

Mukherjee et al., "Sensitization of diabetic and obese mice to insulin by retinoid X receptor agonists," *Nature*, 386: 407–410, (1997).

Parks et al., "Bile Acids: Natural Ligands for an Orphan Nuclear Receptor," *Science Magazine*, 284: 1365–1368, (1999).

Schoonjans et al., "The peroxisome proliferator activated receptors (PPARs) and their effects on lipid metabolism and adipocyte differentiation," *Biochimica et Biophysica Acta*, 1302: 93–109, (1996).

Solomin et al., "Retinoid–X receptor signalling in the developing spinal cord," *Nature*, 395: 398–402, (1998).

Sorensen et al., "Regulation of Peroxisome Proliferator–Activated Receptors," *Vitamins and Hormones*, 54: 121–166, (1998).

Standeven et al., "Mitogenic Effect of Retinoid X Receptor Agonists in Rat Liver," *Biochemical Pharmacology*, 54: 517–524, (1997).

Teng et al., "Identification of Highly Potent Retinoic Acid Receptor χ–Selective Antagonists," *J. Med. Chem.*, 40: 2445–2451 (1997).

Ueno et al., "A novel retinoic acid receptor (RAR)–selective antagonist inhibits differentiation and apoptosis of HL–60 cells: implications of RARχ–mediated signals in myeloid leukemic cells," *Leukemia Research*, 22: 517–525, (1998).

Umemiya, et al., "Retinoid Antagonists," *Reviews*, 116(12): 928–941 (1996).

Umemiya et al., "Regulation of Retinoidal Actions by Diazepinylbenzoic Acids. Retinoid Synergists Which Activate the RXR–RAR Heterodimers," *J. Med. Chem.*, 40: 4222–4234, (1997).

Vuligonda et al., "A New Class of Potent RAR Antagonists: Dihydroanthracenyl, Benzochromenyl and Benzothiochromenyl Retinoids," *Bioorganic & Medicinal Chemistry Letters*, 9: 743–748, (1999).

Willson, et al., "Peroxisome proliferator–activated receptor agonists," *Current Opinion in Chemical Biology* 1:235–241 (1997).

Willson, et al., "Discovery of Ligands for the Nuclear Peroxisome Proliferator–activated Receptors," *Annals New York Academy of Science*, pp. 276–282.

Yoshimura, et al., "A Novel Type of Retinoic Acid Receptor Antagonist: Synthesis and Structure–Activity Relationships of Heterocyclic Ring–Containing Benzoic Acid Derivatives," *J. Med. Chem.*, 38: 3163–3173, (1995).

Zhang et al., "Retinoid X receptor is an auxiliary protein for thyroid hormone and retinoic acid receptors," *Letters To Nature*, 355: 441–446, (1992).

\* cited by examiner

| Marker | Mean | Geo Mean | CV | Median |
|---|---|---|---|---|
| All | 7.01 | 6.53 | 38.21 | 6.73 |
| M1 | *** | *** | *** | --- |
| M2 | 7.05 | 6.61 | 37.49 | 6.73 |

| Marker | Mean | Geo Mean | CV | Median |
|---|---|---|---|---|
| All | 73.39 | 20.52 | 315.72 | 12.86 |
| M1 | 384.14 | 235.15 | 125.20 | 191.10 |
| M2 | 15.40 | 12.76 | 70.60 | 11.55 |

| Marker | Mean | Geo Mean | CV | Median |
|---|---|---|---|---|
| All | 53.41 | 10.44 | 386.57 | 7.50 |
| M1 | 454.48 | 289.85 | 109.71 | 264.16 |
| M2 | 8.84 | 7.41 | 79.63 | 7.23 |

| Marker | Mean | Geo Mean | CV | Median |
|---|---|---|---|---|
| All | 203.90 | 19.95 | 307.70 | 9.65 |

| Marker | Mean | Geo Mean | CV | Median |
|---|---|---|---|---|
| All | 1124.70 | 164.25 | 134.73 | 352.27 |
| M1 | 1809.78 | 1124.20 | 80.10 | 1596.34 |
| M2 | 10.76 | 8.87 | 69.26 | 8.35 |

USE OF RAR ANTAGONISTS AS MODULATORS OF HORMONE MEDIATED PROCESSES

FIELD OF THE INVENTION

The present invention relates to methods for the modulation of nuclear receptor mediated processes. In a particular aspect, the present invention relates to methods for modulating the activity of members of the steroid/thyroid hormone receptor superfamily by relieving the inhibition of hormone mediated processes caused by retinoic acid receptor, or agonists thereof. In another aspect, the present invention relates to methods for inducing hormone mediated processes.

BACKGROUND OF THE INVENTION

A central problem in eukaryotic molecular biology continues to be the elucidation of molecules and mechanisms that mediate specific gene regulation. As part of the scientific attack on this problem, a great deal of work has been done in efforts to identify ligands (i.e., exogenous inducers) which are capable of mediating specific gone regulation. Additional work has been done in efforts to identify other molecules involved in specific gene regulation.

Although much remains to be learned about the specifics of gene regulation, it is known that ligands modulate gene transcription by acting in concert with intracellular components, including intracellular receptors and discrete DNA sequences known as hormone response elements (HREs). The identification of compounds which directly or indirectly interact with intracellular receptors, and thereby affect transcription of hormone-responsive genes, would be of significant value, e.g., for therapeutic applications.

The actions of steroids, retinoids and thyroid hormones are mediated by intracellular nuclear receptors whose coordinate activity defines the physiological response (Mangelsdorf and Evans, *Cell* 83:841–850 (1995)). These receptors are all structurally related and constitute a superfamily of nuclear regulatory proteins that modulate gene expression in a ligand-dependent fashion. Previous studies have demonstrated that the 9-cis retinoic acid receptor (RXR) serves as a common heterodimneric partner for thyroid hormone receptor (TR), retinoic acid receptor (RAR), vitamin D receptor (VDR), *prostanoids (PRAR)*, as well as numerous orphan receptors (Kliewer et al. (1992) *Nature* 355:446–449).

Nuclear hormone receptor heterodimers can be classified into two distinct groups based upon their transcriptional responses to synthetic RXR ligands. So called "permissive" heterodimers such as PPAR:RXR, espond to either RXR and/or PPAR ligands and the two together have, at least, an additive effect (see, e.g., Mukherjee et al., *Nature* 386:407–10 (1997)). In contrast, so called "non-pennissive" heterodimers, such as RAR:RXR, do not respond to RXR ligands unless ligands for RAR are already present, in which case they yield an additive or synergistic response (Apfel et al., *J Biol Chem.* 270(51):30765–72.(1995); Chen et al. *PNAS* 93:7567–7571 (1996)). Other non-permissive heterodimers include TR:RXR and VDR:RXR heterodimers, which also do not appear to be activated by RXR ligands. Indeed, the RXR ligand, LG100268, appears to partially antagonize the action of thyroid hormone.

This difference between permissive and non-permissive heterodimers is likely to be important for regulating the activity of naturally occurring RXR ligands (Heyman et al., *Cell* (1992) 68:397–406; Mascrez et al., *Development* (1998) 125(23):4691–707; Solomin et al., *Nature* (1998) 395(6700):398–402; Fujita and Mitsuhashi, *Biochem Biophys Res Commun* (1999) 255(3):625–30)] as well as being crucial to understanding the behavior of synthetic compounds currently under development as both anti-cancer and anti-diabetic agents (see, e.g., Anzano et al., *Cancer Research* (1994) 54:4614–4617, Gottardis et al., *Cancer Research* (1996) 56:5566–5570, Mukheijee et al., supra). It has been also suggested that RXR can function as a homodimer (Mangelsdorf et al., *Cell* 66(3):555-61 (1991)). By competing for dimerization with RXR on response elements, the relative abundance of RAR and PPAR determines whether the RXR signaling pathway will be functional.

PPARα is a permissive member of the nuclear receptor superfamily, which includes receptors for the steroid, thyroid and retinoid hormones (see Mangelsdorf & Evans in *Cell* 83:841–50 (1995)). Two other PPARα-related genes (PPARγ and PPARδ) have been identified in mammals. PPARγ is highly enriched in adipocytes, while the γ isoform is ubiquitously expressed (see Schoonjans et al., in *Biochim Biophys Acta* 1302:93–109 (1996)). Like other members of this receptor superfamily, all of the PPAR isoforms contain a central DNA binding domain that recognizes response elements in the promoters of their target genes (see, for example, Latruffe et al. in *Biochimie* 79:81–94 (1997)). PPAR response elements (PPRE) are composed of a directly repeating core-site separated by 1 nucleotide (see Kliewer et al., in *Nature* 358:771–4 (1992)). In order to recognize a PPRE, PPARs must heterodimerize with the 9-cis retinoic acid receptor (RXR).

The peroxisome proliferator activated receptors (PPARs) preferentially bind to DNA, i.e., response elements, as heterodimers with a common partner, the retinoid X (or 9-cis retinoic acid) receptor (RXR; see, for example, Kliewer et al., in *Nature* 355:446–449 (1992); Leid et al, in *Cell* 68:377–395 (1992); Marks et al., in EMBO J. 11:1419–1435 (1992); Zhang et al., in *Nature* 355:441–446 (1992); and Issemann et al., in *Biochimie.* 75:251–256 (1993). Once bound to a response element, PPARs activate transcription following binding of ligand to the C-terminal ligand binding domain thereof. Due to the key role of ligands for the activation of transcription, an intense search for the identification of ligands for members of the PPAR family has been undertaken by a number of research groups.

PPARα has been identified as a vertebrate nuclear hormone receptor which regulates genes involved in fatty acid (FA) degradation (δ-and ω-oxidation; see Schoonjans et al., in *Biochim Biophys Acta* 1302:93–109 (1996)). PPARα is highly expressed in the liver and was originally identified by Green and colleagues as a molecule that mediates the transcriptional effects of drugs that induce peroxisome proliferation in rodents (see Issemann & Green in *Nature* 347:645–50 (1990)). Mice lacking functional PPARα are incapable of responding to these agents and fail to induce expression of a variety of genes required for the metabolism of FAs in peroxisomes, mitochondria and other cellular compartments (see Lee et al., in *Mol Cell Biol* 15:3012–3022 (1995)). As a result, PPARα-deficient mice inappropriately accumulate lipid in response to pharmnacologic stimuli.

PPARα appears to regulate FA oxidation, suggesting that PPARα ligands may represent endogenous signals for FA degradation (see Schoonjans et al., supra). Fatty acids (FAs) are ubiquitous biological molecules that are utilized as metabolic fuels, as covalent regulators of signaling molecules and as essential components of cellular membranes.

It is thus logical that FA levels should be closely regulated. Indeed, some of the most common medical disorders in industrialized societies (e.g., cardiovascular disease, hyperlipidemia, obesity and insulin resistance) are characterized by altered levels of FAs or their metabolites (see, for example, Durrington, in *Postgrad Med* J 69 Suppl 1, S18–25; discussion S25–9 (1993) and Reaven, in *J Intern Med Suppl* 736:13–22 (1994)).

PPARγ is preferentially expressed in adipose tissue. PPARγ-activation leads to adipocyte differentiation and improved insulin signaling of mature adipocytes. 15-deoxy-$\Delta^{12,14}$-prostaglandin $J_2$ (15d-$J_2$) has been identified as a ligand for PPARγ (see, for example, Forman et al., in *Cell* 83:803–12 (1995) and Kliewer et al., in *Cell* 83:813–9 (1995)). Activation of PPARγ by 15d-$J_2$ or its synthetic analogs (e.g., thiazolidinediones; see Forman et al., supra) promotes differentiation of pre-adipocytes into mature, triglyceride-containing fat cells. Similarly, thiazolidinediones have been shown to increase body weight in animals (see, e.g., Zhang et al. (1996) *J Biol Chem* 271:9455–9459), suggesting that 15d-$J_2$ may be utilized as an in vivo signal to store fatty acids (FAs) in the form of triglycerides.

Accordingly, there is a need in the art for new agents and compositions which allow the modulation of hormone mediated processes. This and other needs in the art are addressed by the present invention.

BRIEF DESCRIPTION OF THE INVENTION

In accordance with the present invention, it has been discovered that retinoic acid receptor (RAR) antagonists are capable of modulating processes mediated by other members of the steroid/thyroid hormone receptor superfamily, including permissive receptors such as PPARs (e.g., PPARα, PPARδ and PPARγ). Indeed, it has been discovered that RAR antagonists, in combination with agonists for members of the steroid/thyroid hormone receptor superfamily, are capable of inducing and/or enhancing processes mediated by such members.

DETAILED DESCRIPTION OF THE INVENTION

Figure 1:
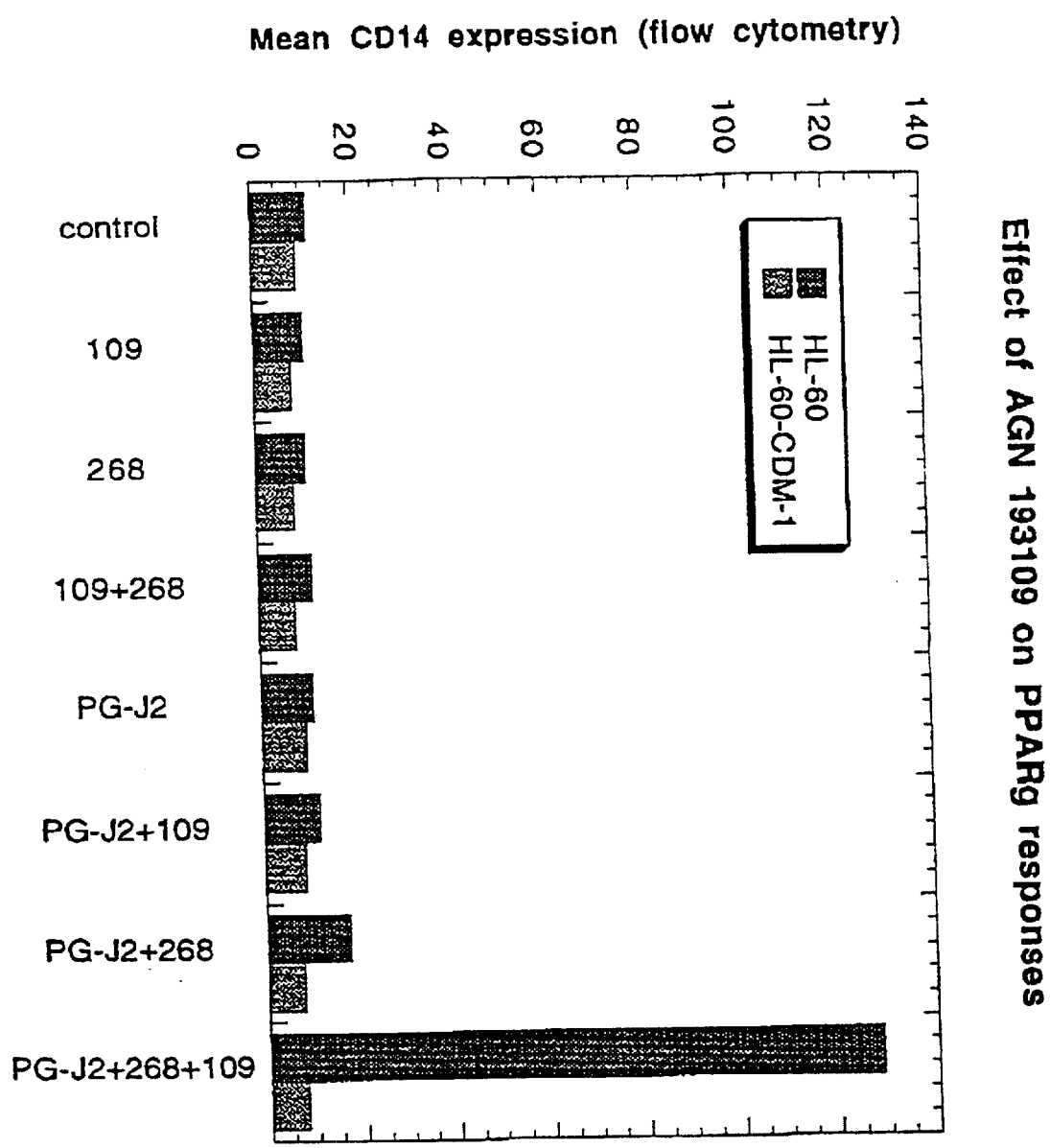
FIG. 1 illustrates the effects of AGN193109 on PPARγ response (induction of CD14 expression in myeloid cell lines), by comparing HL-60 (intact PPARγ response) and HL-60-CDM-1 cells (impaired PPARγ response, wherein no PPARγ is expressed).

In accordance with the present invention, there are provided compositions for modulating hormone mediated process(es) comprising:
  at least one agonist for a member of the steroid/thyroid hormone receptor superfamily, and
  optionally, at least one agonist for a heterodimer partner for said member; and
  at least one antagonist for a second member of the steroid/thyroid hormone receptor superfamily, preferably for a non-permissive member such as RAR.

As employed herein, the phrase "members of the nuclear receptor superfamily" (also known as "members of the steroid/thyroid hormone superfamily of receptors" or "intracellular receptors") refers to hormone binding proteins that operate as ligand-dependent transcription factors, including identified members of the steroid/thyroid hormone superfamily of receptors for which specific ligands have not yet been identified (referred to as hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153), and the like. The highly conserved amino acids of the DNA-binding domain of members of the superfamily are as follows:

Cys-X-X-Cys-X-X-Asp\*-X-Ala\*-X-Gly\*-X-Tyr\*-X-X-X-X-Cys-X-X-Cys-Lys\*-X-Phe-Phe-X-Arg\*-X-X-X-X-X-X-X-X-(X-X-)Cys-X-X-X-X-X-(X-X-)Cys-X-X-X-Lys-X-X-Arg-X-X-Cys-X-X-Cys-Arg\*-X-X-Lys\*-Cys-X-X-X-Gly\*-Met (SEQ ID NO:1);

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Members of the steroid/thyroid hormone superfamily of receptors (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), and the like; plus retinoid receptors, such as the various isoforms of retinoic acid receptor (e.g., RARα, RARβ or RARγ), the various isoforms of retinoid X (or 9-cis retinoic acid) receptor (e.g., RXRα, RXRβ, or RXRγ), various isoforms of peroxisome proliferator-activated receptors (e.g., PPARα, PPARγ, PPARδ) and the like (see, e.g., U.S. Pat. Nos. 4,981,784; 5,171,671; and 5,071,773); thyroid hormone receptor ($T_3R$), such as TRα, TRβ, and the like; steroid and xenobiotic receptor (SXR, see for example, Blumberg et al., *Genes Dev* (1998) 12(20): 3195–205), RXR-interacting proteins (RIPs; see, e.g., Seol et al., *Mol Endocrinol* (1995) 9(1):72–85; Zavacki et al., *Proc Natl Acad Sci USA* (1997) 94(15):7909–14) including farnesoid X receptor (FXR; see for example, Forman et al., *Cell* (1995) 81(5):687–93), BXR (Blumberg et al., *Genes Dev* (1998) 12(9):1269–77), Hanley et al., *J Clin Invest* (1997) 100(3):705–12, O'Brien et al., *Carcinogenesis* (1996) 17(2):185–90), pregnenolone X receptor (PXR; see for example, Schuetz et al., *Mol Pharmacol* (1998) 54(6): 1113–7), liver X receptor (LXR, see, e.g., Peet et al., *Curr Opin Genet Dev* (1998) 8(5):571–5), insect derived receptors such as the ecdysone receptor (EcR), the ultraspiracle receptor (see, for example, Oro et al., in *Nature* 347:298–301 (1990)), and the like; as well as other gene products which, by their structure and properties, are considered to be members of the superfamily, as defined hereinabove, including the various isoforms thereof (see, e.g., Laudet, V., *J Mol Endocrinol* (1997) 19(3):207–26).

In accordance with the present invention, the compositions for modulating hormone mediated process are capable of modulating the activity of complexes comprising homodimeric or heterodimeric member(s) of the steroid/thyroid hormone superfamily of receptors. It is readily recognized that a number of receptors preferentially bind to DNA as homodimers or heterodimers. Homodimeric members of the steroid/thyroid hormone receptor superfamily include GR, TR, RAR, RXR, and the like (see, e.g., Beato et al., *Steroids* 61(4):240–51 (1996)). Alternatively, RAR, VDR, TR, PPAR, SXR, OR1, SBP, LXR, BXR, and the like, preferentially form heterodimers with a common partner, e.g., RXR (see, for example, Dong et al., Biochemistry (1998) 27(30):10691–700; Yu et al., in *Cell* 67:1251–1266 (1991); Bugge et al., in *EMBO J.* 11:1409–18 (1992); Kliewer et al., in *Nature* 355:446–449 (1992); Leid et al, in *Cell* 68:377–395 (1992); Marks et al., in *EMBO J* 11:1419–1435 (1992); Zhang et al., in *Nature* 355:441–446 (1992); and Issemann et al., in *Biochimie.* 75:251–256 (1993). Similarly, other receptors, e.g., EcR, will form heterodimers with the RXR homolog, ultraspiracle. In a preferred embodiment of the present invention, the invention compositions will modulate the activity of permissive heterodimers. Permissive heterodimeric members of the steroid/thyroid hormone receptor superfamily are well known to those skilled in the art and include PPAR:RXR, LXR:RXR, NGFI-B:RXR, NURR1:RXR, FXR:RXR, BXR:RXR, SXR:RXR, and the like.

As employed herein, the term "agonist (or agonist precursor) for a member of the steroid/thyroid hormone superfamily of receptors" (i.e., intracellular receptor) refers to a substance or compound which, in its unmodified form (or after conversion to its "active" form), inside a cell, binds to receptor protein, thereby creating an agonist/receptor complex, which in turn can activate an appropriate hormone response element. An agonist therefore is a compound which acts to modulate gene transcription for a gene maintained under the control of a hormone response element, and includes compounds such as hormones, growth substances, non-hormone compounds that modulate growth, and the like. Agonists include steroid or steroid-like hormone, retinoids, thyroid hormones, pharmaceutically active compounds, and the like. Individual agonists may have the ability to bind to multiple receptors. Preferably, the agonist is for a member which forms a heterodimer (or homodimer) with additional or other members. In a more preferred embodiment, the agonist for a member of the steroid/thyroid hormone superfamily of receptors is an agonist for a permissive receptor, such as PPAR, LXR, RXR interacting proteins (RIPs including, for example, FXR), and the like. In the most preferred embodiment, the agonist is for a member other than retinoic acid receptor.

Agonists for individual members of the steroid/thyroid hormone superfamily of receptor are well known in the art. For example, agonists for retinoids are described in *The Retinoids : Biology, Chemistry, and Medicine* (Sporn, Roberts & Goodman, eds. (Raven Press, 1993), the entire contents of which is hereby incorporated by reference herein).

Peroxisome proliferator-activated receptor (PPAR) agonist(s) contemplated for use herein are well known in the art. See, for example, Peroxisome Proliferators: Unique Inducers of Drug-Metabolizing Enzymes (Pharmacology and Toxicology) David E. Moody (Editor) (July 1994), the entire contents of which are hereby incorporated by reference herein. As readily recognized by those of skill in the art, a variety of PPAR agonists, both synthetic and naturally occurring, can be used in accordance with the present invention. Exemplary PPAR agonists include hypolipidemic drugs, polyunsaturated fatty acids, eicosanoids, thiazolidines (Komers et al., Physiol Res (1998) 47(4):215–25), benzene compounds, anti-inflammatory compounds (NSAIDs), and the like (see, e.g., Tajima et al., W09915520, Collins et al., *J Med Chem* 41(25):5037–54 (1998), Forman et al., Proc Natl Acad Sci U S A (1997) 94(9):4312–7, Willson et al., Curr Opin Chem Biol (1997) 1(2):235–41, Sorensen et al., Vitam Horm (1998) 54:121–66, Berger et al., J Biol Chem (1999) 274(10):6718–25, Wilson et al., Ann N Y Acad Sci (1996) 804:276–83). Preferred PPAR agonists include troglitazone, WY14,643, GW0072, rosiglitazone (BRL 49653), L-764406, 15-deoxy-Delta12, 14-prostaglandin J2 (15d-PGJ2) and oxidized linoleic acid (9- and 13-HODE), (2S)-((2-benzoylphenyl) amino)-3-4-[2-(5-methyl-2-phenyloxazol-4-yl)ethoxy]phenylpropanoic acid, 2(S)-((2-benzoylphenyl)amino)-3,4-[2-(5-methyl-2-pyridin-4-yloxazol-4-yl)ethoxy]phenylpropionic acid, 2(S)-((2-benzoylphenyl)amino)-3-(4-2-[5-methyl-2-(4-methylpiperazin-1-yl)thiazol-4-yl]ethoxyphenyl) propionic acid, (2S)-3-(4-(benzyloxy)phenyl)-2-((1-methyl-3-oxo-3-phenylpropenyl)amino)propionic acid, (2S)-((2-benzoylphenyl)amino)-3-4-[2-(methylpyridin-2-ylamino) ethoxy]phenylpropionic acid, 3-4-[2-(benzoxazol-2-ylmethylamino)ethoxy]phenyl-(2S)-((2-benzoylphenyl) amino)propanoic acid, and the like.

Additional agonists contemplated for use in the practice of the present invention depend on the target receptor and are known to those skilled in the art, including benzoate metabolites for BXR (e.g., Blumberg et al., *Genes Dev.* (1998) 12(9):1269–77), famesoids and bile acids for FXR (e.g., Parks et al., *Science* (1999) 284(5418):1365–8), oxysterols for LXR (e.g., Janowski et al., *Proc Natl Acad Sci U.S. A* (1999) 96(1):266–71), and the like.

The invention composition further optionally comprises at least one agonist for a second member of the steroid/thyroid hormone superfamily of receptors, i.e., a heterodimer partner. Those of skill in the art readily recognize those members which can form heterodimer partners, including RXR, ultraspiracle NGFI-B, NURR1, and the like. RXR agonist(s) contemplated for use herein are well known in the art. See, for example, The Retinoids, supra. As readily recognized by those of skill in the art, a variety of RXR agonists, both synthetic and naturally occuring, can be used in accordance with the present invention. Examplary RXR agonists include 3-substituted (tetramethyltetrahydronaphthyl)carbonylbenzoic acids (Canan Koch et al., J Med Chem (1999) 42(4):742–50), (E,E,E)-7-(1,2,3,4-tetrahydroquinolin-6-yl)-7-alkyl-6-fluoro-3-methylhepta-2,4,6-trienoic acid derivatives (Hibi et al., J Med Chem (1998) 41(17):3245–52), diaryl sulfide retinoid analogs (Beard et al., J Med Chem (1996) 39(18): 3556–63), phytanic acid (Lemotte et al., Eur J Biochem (1996) 236(1):328–33), tricyclic compounds (U.S. Pat. Nos. 5,770,383, 5,770,382 and 5,770,378), trienic compounds (U.S. Pat. No. 5,721,103), and the like (see also, Jiang et al., Biochem Pharmacol (1995) 50(5):669–76), Heyman WO9710819). Preferred RXR agonists include LGD1069 (Bischoff et al., Cancer Res (1998) 58(3):479–84), LG100153, E(-2-[2-(5,6,7,8-Tetrahydro-3,5,5,8,8-pentamethyl-2-naphthyl)propen-1-yl]-4-thiophenecarboxylic acid (AGN 191701), 2-(5,6,7,8-Tetrahydro-5,5,8,8-tetramethyl-2-naphthyl)-2-(4-carboxylphenyl)-1,3-dioxolane (SR11237), Standeven et al., Biochem Pharmacol (1997) 54(4):517–24), HX600 or HX630, and the like.

In accordance with the present invention, the invention compositions will comprise at least one antagonist for members of the steroid/thyroid hormone superfamily of receptors, including antagonists for other non-permissive receptors, such as antagonists for RAR, TR, VDR, and the like. Preferably, the antagonist will be an RAR antagonist. Those of skill in the art will readily recognize antagonists which can be employed in the practice of the present invention. As readily recognized by those of skill in the art, a variety of retinoic acid receptor (RAR) antagonists, both synthetic and naturally occuring, can be used in accordance with the present invention. Examplary RAR antagonists include dicarba-closo-dodecaboranes (Iijima et al., Chem Pharm Bull (Tokyo) (1999) 47(3):398–404), hydroanthracenyl, benzochromenyl and benzothiochromenyl retinoids (Vuligonda et al., Bioorg Med Chem Lett (1999) 9(5):743–8), diarylacetylenes, benzoic acid derivatives (see, e.g., Kagechika, H. (1994) *Yakugaku Zasshi* 114(11):847–862; Eckhardt et al. (1994) *Toxicol Lett* 70(3): 299–308; Yoshimura et al. (1995) *J Med Chem* 38(16): 3163–3173; Chen et al. (1995) *EMBO* 14(6):1187–1197; Teng et al. (1997) *J Med Chem* 40(16):2445–2451); naphthalenyl analogs (see, e.g., Johnson et al. (1995) *J Med Chem* 38(24):4764–4767; Agarwal et al. *J Biol Chem* 271 (21):12209–12212: Umemiya et al. (1996) *Yakugaku Zasshi* 116(12):928–941); aryl-substituted and aryl and (3-oxo-1-propenly)-substituted benzopyran, benzothiopyran, 1,2-dihydroquinoline, and 5,6-dihydronaphthalene derivatives (Klein et al. U.S. Pat. Nos. 5,877,207 and 5,776,699), adamantyl-substituted biaromatic compounds (Bernardon and Charpentier, U.S. Pat. No. 5,877,342), 1-phenyl-adamantane derivatives (Bernardon and Bernardon EP 776885), polyaromatic heterocyclic compounds (Charpentier et al. U.S. Pat. No. 5,849,798), dihydronaphthalene derivatives (Beard et al., U.S. Pat. No. 5,808,124 and Johnson et al. U.S. Pat. No. 5,773,594), 4-phenyl (benozopyranoyl or naphthoyl) amidobenzoic acid derivatives (Chandraratna et al. WO 98/US/13065), diazepinylbenzoic acid derivatives (Umemiya et al., J Med Chem (1997) 40(26):4222–34), tetrahydronaphthalene derivatives (Vuligonda et al. U.S. Pat. No. 5,763,635, 5,741,896 and 5,723,666), aryl-and heteroarylcyclohexenyl substituted alkenes (Beard et al. U.S. Pat. No. 5,760,276), dibenzofiran compounds, including aromatic dibenzofuran compounds (Charpentier et al. U.S. Pat. No. 5,702,710, Charpentier and Bernard U.S. Pat. No. 5,747,530), N-aryl substituted tetrahydroquinolines (Beard et al. U.S. Pat. No. 5,739,338), benzo[1,2-g]-chrom-3-ene and benzo[1,2-g]-thiochrom-3-ene derivatives (Vuligonda et al. U.S. Pat. No. 5,728,846), and the like (see also, Chandraratna, RA, Cutis (1998) 61(2 Suppl):40–5).

Examples of specific RAR antagonists contemplated for use herein include LE135 (Umemiya et al. (1996) *Yakugaku Zasshi* 116(12):928–941), LE511, LE540, LE550 (Li et al., *J Biol Chem* (1999) 274(22):15360–6; Umemiya et al. (1996) *Yakugaku Zasshi* 116(12):928–941), Ro41-5253 (Keidel et al. (1994) *Mol Cell Biol* 14(1):287–298), SR11330, SR11334, SR11335 (Lee et al. (1996) *J Biol Chem* 271(20):11897–11903), BMS453, BMS411 (Chen et al. (1995) *EMBO* 14(6):1187–1197), CD2366 and CD2665 (Meister et al., *Anticancer Res.* (1998) 18(3A):1777–1786), ER27191 (Uemo et al., *Leuk. Res.* (1998) 22(6):517–525), AGN 193109 (Johnson et al., *Bioorg Med Chem Lett* (1999) 9(4):573–6), 4-[4,5,7,8,9,10-hexahydro-7, 7,10,-10-tetramethyl-1-(3-pyridylmethyl)anthra[1,2-b]pyrrol-3-yl] benzoic acid, 4-[4,5,7,8,9,10-hexahydro-7,7,10,10-tetramethyl-1-(3-pyridylmethyl)-5-thiaanthral[1,2-b]pyrrol- 3-yl]benzoic acid, 4-[4,5,7,8,9,10-hexahydro-7,7,10,10-tetramethyl-1-(3-pyridyhnethyl)anthra[2,1-d]pyrazol-3-yl] benzoic acid (Yoshimura et al. (1995) *J Med Chem* 38(16): 3163–3173), AGN193109 (Agarwal et al. *J Biol Chem* 271(21):12209–12212), and the like. A presently preferred class of RAR antagonists contemplated for use according to the invention are aryl dihydronaphthalenyl derivatives of acetylene. An especially preferred RAR antagonist contemplated for use herein is 4-[[5,6-dihydro-5,5-dimethyl-8-(4-methylphenyl)-2-naphthalenyl]ethynyl]benzoic acid.

In accordance with another aspect of the present invention, there are provided methods for modulating hormone mediated processes, the methods comprising introducing an effective amount of at least one retinoic acid receptor (RAR) antagonist in combination with at least one agonist for the member into the system. Preferably, the agonist is an agonist for a member of the steroid/thyroid hormone superfamily of receptors which form heterodimers or homodimers with other or additional members. More preferably, the agonist is for a permissive receptor. In the presently most prefered embodiment, the agonist is not for retinoic acid receptor.

In yet another preferred embodiment of the present invention, there are provided methods for relieving, in a biological system, the inhibition of hormone mediated process(es), such as process(es) mediated by peroxisome proliferator activated receptor(s) (PPARs). In a presently preferred aspect, the invention method relieves inhibition of hormone mediated processes caused by retinoic acid receptor (RAR) and agonist(s) thereof. Alternatively, or in addition, there are provided methods for inducing hormone mediated process(es) in a biological system by peroxisome proliferator activated receptor(s) (PPARs). Invention methods comprise introducing an effective amount of at least one retinoic acid receptor (RAR) antagonist, alone, or in combination with PPAR agonists, into said system.

In accordance with yet another embodiment of the present invention, the invention method further comprises administering or co-administering an effective amount of at least one agonist for a heterodimer partner for the member, e.g., RXR, NURR1, ultraspiracle, and the like.

As employed herein, the term "modulate" refers to the ability of compound(s) to either directly (by binding to the receptor as a ligand) or indirectly (by relieving the inhibition of process(es) mediated by members of the steroid/thyroid hormone receptor superfamily, or as a precursor and/or facilitator for a ligand or an inducer which promotes production of ligand from a precursor, or combinations thereof) induce and/or enhance expression of gene(s) maintained under hormone expression control, or to repress expression of gene(s) maintained under such control.

As employed herein, the phrase "relieving . . . the inhibition of process(es) . . . " refers to the ability of a suitable compound, e.g., RAR antagonist, to either directly (by binding to the receptor as a ligand) or indirectly (as a precursor for a ligand or an inducer which promotes production of ligand from a precursor) counteract or divert the ability of members of the steroid/thyroid hormone receptor superfamily, and agonists thereof, to inhibit or interfere with the expression of gene(s) maintained under hormone expression control. Preferably, members of the steroid/thyroid hormone receptor superfamily contemplated for use in the practice of the present invention include non-permissive receptors such as retinoic acid receptor.

As employed herein, the term "inducing" refers to the ability of a modulator for a member of the steroid/thyroid hormone receptor superfamily to either directly (by binding to the receptor as a ligand) or indirectly (as a precursor for a ligand or an inducer which promotes production of ligand from a precursor) promote expression of gene(s) maintained under hormone expression control.

As employed herein, the phrase "biological system" refers to an intact organism or a cell-based system containing the various components required for response to the ligands described herein, e.g., a member of the steroid/thyroid hormone receptor superfamily, a heterodimer partner for the member (e.g., RXR), and a reporter responsive to the heterodimer (which typically comprises a response element (RE) in operative communication with a reporter gene; suitable reporters include luciferase, chloramphenicol transferase, β-galactosidase, and the like).

As employed herein, the phrase "hormone mediated processes" refers to biological, physiological, endocrinological, and other bodily processes which are mediated by receptor or receptor combinations which are responsive to the ligands described herein. Modulation of such processes can be accomplished in vitro or in vivo. In vivo modulation can be carried out in a wide range of subjects, such as, for example, humans, rodents, sheep, pigs, cows, and the like. Exemplary processes contemplated to be modulated include neoplastic diseases, inflammatory or infectious diseases, and the like.

As employed herein, the phrase "process(es) mediated by peroxisome proliferator activated receptor(s) (PPARs)" refers to processes which are manifested by expression or repression of expression of PPAR-responsive genes. Thus, for example, "PPARα-responsive genes" refers to genes whose expression products are involved in the biological, physiological, endocrinological, and other bodily processes which are mediated by receptor or receptor combinations which are responsive to the PPARα ligands described herein (e.g., genes involved in fatty acid metabolism in peroxisomes, mitochondria and other cellular compartments (including FA degradation (by β-and ω-oxidation), and the like). Modulation of such processes can be accomplished in vitro or in vivo. In vivo modulation can be carried out in a wide range of subjects, such as, for example, humans, rodents, sheep, pigs, cows, and the like.

As employed herein, the phrase "PPARδ-responsive genes" refers to genes whose expression products are involved in the biological, physiological, endocrinological, and other bodily processes which are mediated by receptor or receptor combinations which are responsive to PPARδ ligands. Modulation of such processes can be accomplished in vitro or in vivo. In vivo modulation can be carried out in a wide range of subjects, such as, for example, humans, rodents, sheep, pigs, cows, and the like.

As employed herein, the phrase "PPARγ-responsive genes" refers to genes whose expression products are involved in the biological, physiological, endocrinological, and other bodily processes which are mediated by receptor or receptor combinations which are responsive to PPAR-γ ligands (e.g., cell differentiation to produce lipid-accumulating cells, regulation of insulin-sensitivity and blood glucose levels, especially as related to hypoglycemia/hyperinsulinism (resulting, for example, from abnormal pancreatic beta-cell function, insulin-secreting tumors and/or autoimmune hypoglycemia due to autoantibodies to insulin, the insulin receptor or autoantibodies that are stimulatory to pancreatic beta-cells), the formation of macrophages which lead to the development of atherosclerotic plaques, and the like). Modulation of such processes can be accomplished in vitro or in vivo. In vivo modulation can be carried out in a wide range of subjects, such as, for example, humans, rodents, sheep, pigs, cows, and the like.

As employed herein, the phrase "effective amount" refers to levels of compound sufficient to provide circulating concentrations high enough to modulate the expression of an isoform of PPAR. Such a concentration typically falls in the range of about 10 nM up to 2 mM; with concentrations in the range of about 100 nM up to 500 nM being preferred. Since the activity of different compounds described herein may vary considerably, and since individual subjects may present a wide variation in severity of symptoms, it is up to the practitioner to determine a subject's response to treatment and vary the dosages accordingly.

The above-described biologically active compounds can be administered in a variety of forms (e.g., in combination with a pharmaceutically acceptable carrier therefor) and by a variety of modes of delivery. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

As used herein, co-administration of two pharmnacologically active compounds refers to the delivery of two separate chemical entities, whether in vitro or in vivo. Co-administration refers to the simultaneous delivery of separate agents; to the simultaneous delivery of a mixture of agents; as well as to the delivery of one agent followed by delivery of the second agent. In all cases, agents that are co-administered are intended to work in conjunction with each other.

Each of the references and U.S. and foreign patents cited herein are hereby incorporated by reference in its entirety. The invention will now be described in greater detail by reference to the following non-limiting examples.

EXAMPLE 1

Cell Culture and Transfection

CV-1 cells were grown and transfected as described by Forman et al., in *Cell* 83:803–12 (1995). The reporter construct, PPREx3 TK-LUC, contained 3 copies of the acyl CoA oxidase PPRE upstream of the Herpes virus thymidine kinase promoter (see Kliewer et al., in *Nature* 358:771–4 (1992)). Expression vectors contained the cytomegalovirus IE promoter/enhancer (pCMX) upstream of wild-type mouse PPARα, mouse PPARγ1-DN (Met$^{105}$-Tyr$^{475}$), mouse PPARα*-DN (Leu$^{69}$-Tyr$^{440}$), mouse PPARα-G (Glu$^{282}$->Gly) (see Hsu et al., in *Mol Pharmacol* 48:559–67 (1995))

or *E. coli* β-galactosidase as an internal control. Cells were exposed to the compounds for 24 hours then harvested and assayed for luciferase and β-galactosidase activity. All points were performed in triplicate and varied by less than 10%. Normalized luciferase activity was determined and plotted as fold-activation relative to untreated cells. Each experiment was repeated three or more times with similar results.

EXAMPLE 2

Electrophoretic Mobility Shift Assays

In vitro translated mouse PPARα (0.2 ml) and human RXRα (0.1 ml) were incubated for 30 minutes at room temperature with 100,000 cpm of Klenow-labeled acyl CoA oxidase PPRE as described by Forman et al., in *Cell* 81:687–93 (1995), but with 150 mM KCl.

EXAMPLE 3

Activation of PPARα by Diarlacetlenes

In order to evaluate the ability of RAR antagonists to relieve the inhibition of processes mediated by PPARs, CV-1 cells are transiently transfected with a PPAR responsive reporter, PPAR expression vectors and then treated with 4-[[5,6-dihydro-5, 5-dimethyl-8-(4-methylphenyl)-2-naphthalenyl]ethynyl]benzoic acid. Wy 14,643 and rosiglitazone (BRL 49653) are included as positive controls since these compounds selectively activate PPAR a and y, respectively (see Forman et al., in *Cell* 83:803–12 (1995), Kliewer et al., in *Cell* 83:813–9 (1995) and Kliewer et al., in *Proc Natl Acad Sci USA* 91:7355–9 (1994)).

4-[[5,6-dihydro-5,5-dimethyl-8-(4-methylphenyl)-2-naphthalenyl]ethynyl]benzoic acid is found to activate PPARα maximally at about 300 mM.

EXAMPLE 4

Activation of PPARα by Benzoic Acid Derivatives

In order to evaluate the ability of RAR antagonists to relieve the inhibition of processes mediated by PPARs, CV-1 cells are transiently transfected with a PPAR responsive reporter, PPAR expression vectors and then treated with 4-[4-(2,2,2,-trifluoro-1-methoxyethyl)5,6,7,8-tetrahydro-5,5,8,8-tetramethyl-2-anthracenyl]benzoic acid (SR11335; Lee et al. *J Biol Chem* 271:11897–11903). Wy 14,643 and BRL 49653 are included as positive controls since these compounds selectively activate PPAR α and γ, respectively (see Forman et al., in *Cell* 83:803–12 (1995), Kliewer et al., in *Cell* 83:813–9 (1995) and Kliewer et al., in *Proc Natl Acad Sci USA* 91:7355–9 (1994)).

4-[4-(2,2,2,-trifluoro-1-methoxyethyl)5,6,7,8-tetrahydro-5,5,8,8-tetramethyl-2-anthracenyl]benzoic acid is found to activate PPARα maximally at about 300 mM.

EXAMPLE 5

Retinoid Antagonists Relieve the Retinoic Acid Induced Inhibition of PPAR Mediated Processes To confirm the effect of an RAR antagonist on PPARα/RXRα, studies are done with the homologous malic enzyme gene promoter (pMECAT −490/+31; see Castelein et al. (1994) *J Biol Chem* 269:26754–26758). The −490/+31 malic enzyme promoter sequence is inserted in a pOCAT2 reporter and used in this transfection experiment with receptor plasmids in COS cells. Increasing amounts of an RAR agonist (e.g., retinoic acid) is presented with a constant amount of PPARα/RARα expressing vectors. The cells are treated with either DMSO, ciprofibrate (100 mM) or with the combination of ciprofibrate and an RAR antagonist.

The activity of the pOCAT2 reporter is reduced alone in the presence of an RAR agonist. PPARα/RXRα stimulate CAT activity of the pMECAT reporter to almost the same extent, regardless of the absence or presence of their respective ligands. RAR agonists suppress CAT activation by the non-liganded PPARα/RARα in a dose dependent manner, and, to a lesser extent, also suppress CAT activation by the ciprofibrate activated receptors. However, RAR agonist is completely unable to counteract PPARα/RARα activated by ciprofibrate and an RAR antagonist. These results show that RAR antagonists may relieve the repression of PPARα transactivation caused by RAR agonist.

EXAMPLE 6

RAR Antagonists Enhances PPARγ Mediated Biological Processes

A myeloid cell line HL-60 was treated with the PPAR gamnma activator, PG-J2 (5 μM), the RXR activator, LG 268 (100 nM), the RAR/RXR activator, 9-cis retinoic acid (100 nM), and the RAR antagonist AGN 193109 (100 nM), individually or in different combinations. The expression levels of monocytic cell surface marker CD14 is measured over two days. As a comparison, HL-60-CDM-1 cells which do not express PPARγ and thus have impaired PPARγ response, were also treated with the above ligands, individually or in various combinations (FIG. 1).

Figure 2:
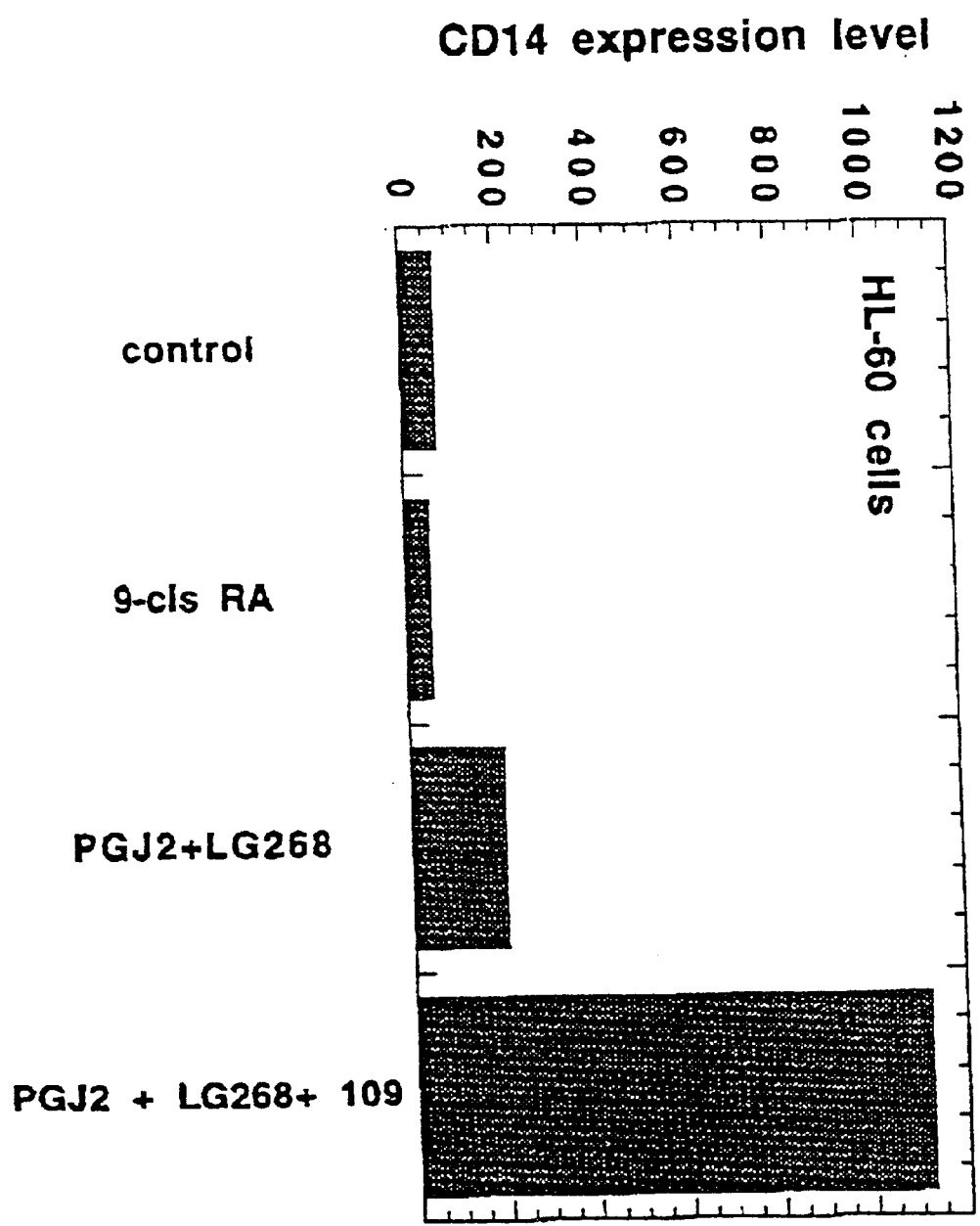
FIG. 2 illustrates the effects of the combination of the PPAR-γ agonist, PG-J2, the RXR agonist, LG 268, and the RAR antagonist, AGN 193109, on HL-60 cells.
Figure 3:
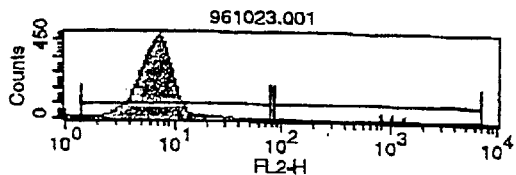
FIG. 3 provides several graphs summarizing the flow cytometry data for experiments depicted in FIG. 2.
Figure 3:
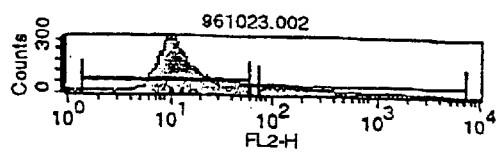
Figure 3:
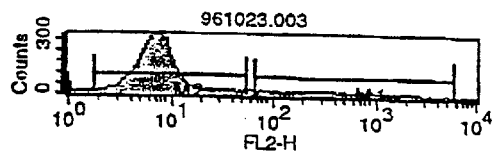
Figure 3:
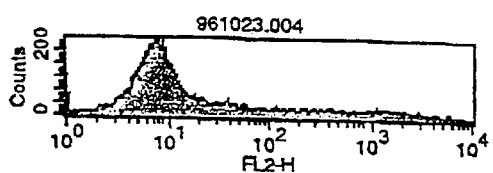
Figure 3:
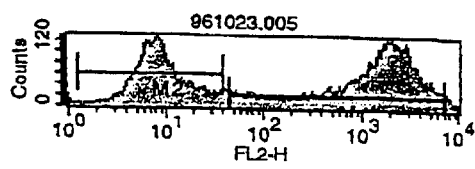

FIGS. 1 and 2 illustrate the dramatic effect of the combination of PPAR-γ ligand, PG-J2, the RXR agonist, LG268, and the RAR antagonist, AGN193109, on HL-60 cells.

While the invention has been described in detail with reference to certain preferred embodiments thereof, it will be understood that modifications and variations are within the spirit and scope of that which is described and claimed.

That which is claimed is:

1. A synergistic composition for modulating hormone mediated process(es) comprising an effective amount of:
   at least one agonist for a member of the steroid/thyroid hormone receptor superfamily,
   at least one RAR antagonist, and
   at least one agonist for a heterodimer partner for said member.

2. A composition according to claim 1, wherein said member of the steroid/thyroid hormone receptor superfamily is a permissive receptor.

3. A composition according to claim 2, wherein said permissive receptor is PPAR, NGFI-B, NURR1, FAR or LXR.

4. A composition according to claim 3, wherein said agonist for said permissive receptor is a PPAR agonist.

5. A composition according to claim 4, wherein said PPAR agonist is a hypolipidemic drug, a polyunsaturated fatty acid, an eicosanoid, a thiazolidine, a benzene compound, an anti-inflammatory compound (NSAID), or mixtures thereof.

6. A composition according to claim 5, wherein said PPAR agonist is troglitazone, WY14,643, GW0072, rosiglitazone (BRL 49653), L-764406, 15-deoxy-Delta12, 14-prostaglandin J2 (15d-PGJ2) and oxidized linoleic acid (9- and 13-HODE), (2S)-((2-benzoylphenyl)amino)-3-4-[2-(5-methyl-2-phenyloxazol-4-yl)ethoxy]phenylpropanoic acid, 2(S)-((2-benzoylphenyl)amino)-3,4-[2-(5-methyl-2-pyridin-4-yloxazol-4-yl)ethoxy]phenylpropionic acid, 2(S)-((2-benzoylphenyl)amino)-3-(4-2-[5-methyl-2-(4-methylpiperazin-1-yl)thiazol-4-yl]ethoxyphenyl)propionic acid, (2S)-3-(4-(benzyloxy)phenyl)-2-((1-methyl-3-oxo-3-phenylpropenyl)amino)propionic acid, (2S)-((2-benzoylphenyl)amino)-3-4-[2-(methylpyridin-2-ylamino) ethoxy]phenylpropionic acid, 3-4-[2-(benzoxazol-2-ylmethylamino)ethoxy]phenyl-(2S)-((2-benzoylphenyl) amino)propanoic acid, or mixtures thereof.

7. A composition according to claim 4 wherein said PPAR agonist is an agonist for PPAR-α.

8. A composition according to claim 4 wherein said PPAR agonist is an agonist for PPAR-δ.

9. A composition according to claim 4 wherein said PPAR agonist is an agonist for PPAR-γ.

10. A composition according to claim 1, wherein said heterodimer partner is RXR or ultraspiracle.

11. A composition according to claim 10, wherein said agonist for said heterodimer partner is an RXR agonist.

12. A composition according to claim 11, wherein said RXR agonist is a 3-substituted (tetramethyltetrahydronaphthyl)carbonylbenzoic acid, an (E,E,E)-7-(1,2,3,4-tetrahydroquinolin-6-yl)-7-alkyl-6-fluoro-3-methylhepta-2,4,6-trienoic acid derivative, a diaryl sulfide retinoid analog, phytanic acid, a tricyclic or trienic compound, or mixtures thereof.

13. A composition according to claim 1, wherein said RAR antagonist is a dicarba-closo-dodecaborane, a hydroanthracenyl, a benzochromenyl and/or a benzothiochromenyl retinoid, a diarylacetylene, a benzoic acid derivative; naphthalenyl analog, an aryl-substituted, aryl and/or (3-oxo-1-propenly)-substituted benzopyran, a benzothiopyran, a 1,2-dihydroquinoline, a 5,6-dihydronaphthalene derivatives, an adamantyl-substituted biaromatic compound, a 1-phenyl-adamantane derivative, a polyaromatic heterocyclic compound, a dihydronaphthalene derivative, a 4-phenyl(benozypyranoyl or naphthoyl) amidobenzoic acid derivative, a diazepinylbenzoic acid derivative, a tetrahydronaphthalene derivative, an aryl- or heteroarylcyclohexenyl substituted alkene, a dibenzofuran compound, a N-aryl substituted tetrahydroquinolines, a benzo[1,2-g]-chrom-3-ene or benzo[1,2-g]-thiochrom-3-ene derivative, an aryl dihydronaphthalenyl derivative of acetylene, or mixtures thereof.

14. A composition according to claim 1, wherein said RAR antagonist is LE135, LE511, LE540, LE550, Ro41-5253, SR11330, SR11334, SR11335, BMS453, BMS411, CD2366, CD2665, ER27191, AGN193109, 4-[4,5,7,8,9,10-hexahydro-7,7,10,10-tetramethyl-1-(3-pyridylmethyl) anthra[1,2-b]pyrrol-3-yl]benzoic acid, 4-[4,5,7,8,9,10-hexahydro-7,7,10,10-tetramethyl-1-(3-pyridyhnethyl)-5-thiaanthral[1,2-b]pyrrol-3-yl]benzoic acid, 4-[4,5,7,8,9,10-hexahydro-7,7,10,10-tetramethyl-1-(3-pyridylmethyl) anthra[2,1-d]pyrazol-3-yl]benzoic acid, AGN193109, 4-[[5,6-dihydro-5,5-dimethyl-8-(4-methylphenyl)-2-naphthalenyl]ethynyl]benzoic acid, or mixtures thereof.

* * * * *

UNITED STATES PATENT AND TRADEMARK OFFICE
CERTIFICATE OF CORRECTION

PATENT NO.   : 6,436,993 B1 Page 1 of 1
DATED        : August 20, 2002
INVENTOR(S)  : Ronald M. Evans, Peter J. Tontonoz and Laszlo Nagy It is certified that error appears in the above-identified patent and that said Letters Patent is hereby corrected as shown below:

Column 16,
Line 49, change "pyridyhnethyl" to -- pyridylmethyl --

Signed and Sealed this

Twenty-first Day of October, 2003

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 71
<212> TYPE: PRT
<213> ORGANISM: Artificial Sequence
<220> FEATURE:
<223> OTHER INFORMATION: general sequence for DNA binding domain for
    members of the steroid/thyroid hormone receptor
    superfamily

```
<220> FEATURE:
<221> NAME/KEY: VARIANT
<222> LOCATION: (2)...(3)
<223> OTHER INFORMATION: each Xaa designates non-conserved amino acids
<220> FEATURE:
<221> NAME/KEY: VARIANT
<222> LOCATION: (5)...(6)
<223> OTHER INFORMATION: each Xaa designates non-conserved amino acids
<220> FEATURE:
<221> NAME/KEY: VARIANT
<222> LOCATION: (8)...(8)
<223> OTHER INFORMATION: each Xaa designates non-conserved amino acids
<220> FEATURE:
<221> NAME/KEY: VARIANT
<222> LOCATION: (10)...(10)
<223> OTHER INFORMATION: each Xaa designates non-conserved amino acids
<220> FEATURE:
<221> NAME/KEY: VARIANT
<222> LOCATION: (12)...(12)
<223> OTHER INFORMATION: each Xaa designates non-conserved amino acids
<220> FEATURE:
<221> NAME/KEY: VARIANT
<222> LOCATION: (14)...(17)
<223> OTHER INFORMATION: each Xaa designates non-conserved amino acids
<220> FEATURE:
<221> NAME/KEY: VARIANT
<222> LOCATION: (19)...(20)
<223> OTHER INFORMATION: each Xaa designates non-conserved amino acids
<220> FEATURE:
<221> NAME/KEY: VARIANT
<222> LOCATION: (23)...(23)
<223> OTHER INFORMATION: each Xaa designates non-conserved amino acids
<220> FEATURE:
<221> NAME/KEY: VARIANT
<222> LOCATION: (26)...(26)
<223> OTHER INFORMATION: each Xaa designates non-conserved amino acids
<220> FEATURE:
<221> NAME/KEY: VARIANT
<222> LOCATION: (28)...(38)
<223> OTHER INFORMATION: each Xaa designates non-conserved amino acids;
    37-38 are optional residues
<220> FEATURE:
<221> NAME/KEY: VARIANT
<222> LOCATION: (40)...(47)
<223> OTHER INFORMATION: each Xaa designates non-conserved amino acids;
    45-47 are optional residues
<220> FEATURE:
<221> NAME/KEY: VARIANT
<222> LOCATION: (49)...(51)
<223> OTHER INFORMATION: each Xaa designates non-conserved amino acids
<220> FEATURE:
<221> NAME/KEY: VARIANT
<222> LOCATION: (53)...(54)
<223> OTHER INFORMATION: each Xaa designates non-conserved amino acids
<220> FEATURE:
<221> NAME/KEY: VARIANT
<222> LOCATION: (56)...(57)
<223> OTHER INFORMATION: each Xaa designates non-conserved amino acids
<220> FEATURE:
<221> NAME/KEY: VARIANT
<222> LOCATION: (59)...(60)
<223> OTHER INFORMATION: each Xaa designates non-conserved amino acids
<220> FEATURE:
<221> NAME/KEY: VARIANT
<222> LOCATION: (63)...(64)
<223> OTHER INFORMATION: each Xaa designates non-conserved amino acids
<220> FEATURE:
<221> NAME/KEY: VARIANT
<222> LOCATION: (67)...(69)
<223> OTHER INFORMATION: each Xaa designates non-conserved amino acids

<400> SEQUENCE: 1

Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa
            20                  25                  30
```

-continued

```
Xaa Xaa Xaa Xaa Xaa Xaa Cys Xaa Xaa Xaa Xaa Xaa Xaa Xaa Cys
            35              40                  45

Xaa Xaa Xaa Lys Xaa Xaa Arg Xaa Xaa Cys Xaa Xaa Cys Arg Xaa Xaa
        50              55              60

Lys Cys Xaa Xaa Xaa Gly Met
65                  70
```